(12) United States Patent
Dolina et al.

(10) Patent No.: US 7,745,426 B2
(45) Date of Patent: Jun. 29, 2010

(54) COMPOSITIONS AND METHODS FOR REDUCING THE RISK OF EPILEPTIC OCCURRENCE AND/OR FOR TREATMENT OF SEIZURE DISORDERS

(75) Inventors: Svetlana Dolina, Rehovot (IL); Vitaly Shteiman, Tel Aviv (IL); Marina Vinnikova, Ramla (IL); Israel Shapiro, Ramla (IL)

(73) Assignees: D-Pharm Ltd., Kiryat Weizmann Science Park Rehovot (IL); Advanced Neuroprotective Systems Ltd., Kiryat Weizmann Science Park Nes Ziona (IL)

( * ) Notice: Subject to any disclaimer, the term of this patent is extended or adjusted under 35 U.S.C. 154(b) by 1133 days.

(21) Appl. No.: 10/568,152

(22) PCT Filed: Aug. 12, 2004

(86) PCT No.: PCT/IL2004/000745

§ 371 (c)(1),
(2), (4) Date: Mar. 20, 2006

(87) PCT Pub. No.: WO2005/016228

PCT Pub. Date: Feb. 24, 2005

(65) Prior Publication Data

US 2006/0235000 A1    Oct. 19, 2006

(30) Foreign Application Priority Data

Aug. 14, 2003 (IL) .......................... 157397

(51) Int. Cl.
  *A61K 31/44* (2006.01)
  *C07D 403/02* (2006.01)
(52) U.S. Cl. .......... 514/217; 514/221; 514/270; 514/312; 514/340; 514/350; 514/351; 540/504; 540/589; 544/310; 546/156; 546/272.7; 546/299; 546/300

(58) Field of Classification Search ........... None
See application file for complete search history.

(56) References Cited

FOREIGN PATENT DOCUMENTS

| WO | WO 95/31194 | 11/1995 |
| WO | 0156609 | 8/2001 |
| WO | WO 01/56609 A1 | 8/2001 |

OTHER PUBLICATIONS

Dolina et at, Epilepsia (1993), 34(1), 33-42.*
Dakshinamurti et al, Biochimica et Biophysica Acta, Proteins and Proteomics, (2003), 1647(1-2), 225-229.*
Mueller, S.G. et al. "Influence of pyridoxal 5'-phosphate alone and in combination with vigabatrin on brain GABA measured by 1H-NMR-spectroscopy" *Brain Research Bulletin*, vol. 55, No. 4, pp. 555-560 (2001).
Takuma, Yuichi et al. "ACTH Therapy for Infantile Spasms: A Combination Therapy with High-Dose Pyridoxal Phosphate and Low-Dose ACTH" *Epilepsia*, vol. 39, Suppl. 5, pp. 42-45 (1998).
Supplementary Partial European Search Report issued in corresponding European Patent Application No. EP 04 77 0425.

* cited by examiner

*Primary Examiner*—Zinna N Davis
(74) *Attorney, Agent, or Firm*—Davidson, Davidson & Kappel, LLC

(57) ABSTRACT

The present invention relates to compounds and compositions useful for reducing the risk of epileptic occurrences and/or for alleviating epileptic phenomena in patients. In accordance with the invention, the compounds and compositions have at least the following two components: a) vitamin B6-based component selected from pyridoxal, pyridoxamine, pyridoxine, their pharmaceutically acceptable functional derivatives and salts; and b) at least one antiepileptic drug (AED) or anticonvulsive, neuro-protective drug or nootrope compound or moiety. The invention further relates to methods for preventing epileptic episodes and for alleviating epileptic episodes, as well as methods for reducing side effects of antiepileptic drugs.

8 Claims, 3 Drawing Sheets

COMPOSITIONS AND METHODS FOR REDUCING THE RISK OF EPILEPTIC OCCURRENCE AND/OR FOR TREATMENT OF SEIZURE DISORDERS

CONTINUING DATA

This application is a 371 of PCT/IL04/00745 filed Aug. 12, 2004.

FIELD OF THE INVENTION

The present invention relates to compositions and methods of using such compositions for the treatment and prevention of epilepsy and related disorders.

BACKGROUND OF THE INVENTION

Epilepsy is one of the most common chronic neurological disorders. The disease is characterized by recurrent seizures, which originate from abnormal and excessive activity of cerebral neurons and result in a paroxysmal disorganization of brain function. Types of epilepsy include partial (symptomatic) and generalized idiopathic seizures. Partial epilepsy is "localization related" and originates in a limited area of the brain. The generalized form of epilepsy is not caused by a specific brain lesion or disease, other than a possible genetic propensity to generate seizures. Generalized, or grand mal, seizures include tonic-clonic seizures, in which the entire body undergoes convulsions. Left untreated, epilepsy can degenerate into status epilepticus, a potentially fatal neurological emergency [*Antiepileptic Drugs*; eds. R. H. Levy, R. H. Mattson and B. S. Meidrum; 4th Edition, Raven Press, NY, N.Y.; Aicardi. *Epilepsy in children*. 2nd edition. New York: Raven Press, 1994: 18-43]. Idiopathic epilepsy appears to be a heritable disorder though little is known about the precise genetic or biochemical defects involved (Andermann In *Genetic Basis of the Epilepsies*, eds. Anderson V E, Hauser W A, Penry J K, Sing C F. New York: Raven Press 1982: 355-74; Anderson E V, Hauser W A. Genetics. In: Dam M, Gram L, ed. *Comprehensive Epileptology*. New York: Raven Press 1990:57-76). Recent research has indicated the possibility of genetic predisposition to the development of localization-related epilepsy, in particular post-traumatic epilepsy. In this type of epilepsy, a head injury is the resolving exogenous factor inducing the disease with a low penetration of the pathological hereditary factor.

Over 53 million people worldwide suffer from epilepsy, with 2.5 million who have had, or who will have seizures at some point in the U.S. alone. Epilepsy primarily affects children and young adults. Almost 50% of new epilepsy cases occur prior to age 25. About 28% of epileptic patients have intractable epilepsy that is resistant to antiepileptic treatment. A wide spectrum of antiepileptic drugs is used for epilepsy treatment [*Antiepileptic Drugs*; eds. R. H. Levy, R. H. Mattson and B. S. Meldrum; 4th Edition, Raven Press, NY, N.Y.; Aicardi, Epilepsy in children, 2d Edition, Raven Press, 1994]. Nevertheless, a goal, that was expressed 10 years ago (Drugs and Market Development, 1992, v.2, N3), namely to develop antiepileptic drugs (AEDs) which are equally effective yet less toxic than the AEDs currently on the market, has not been accomplished.

One specific form of epilepsy, known as "pyridoxine-dependent epilepsy" has been described as a rare (1:100 000) autosomal recessive genetic disorder that causes severe convulsions with subsequent mental retardation in neonates and infants (Hunt et al. *Pediatrics* 1954; 13:140; Rosenberg In: *Medical Genetics* McKusic V A, ed. 1995: 73-8; Shideler *Am. J. Med. Technol.* 1983; 49:17-22 ; Scriver and Hutchison *Pediatrics* 1963; 31:240-50).

It was reported in the art that pyridoxine-dependent epilepsy can be treated by administration of pyridoxine (Aicardi, Epilepsy in children, 2d Edition, Raven Press 1994; Epilepsy *Problems Solving in Clinical Practice*; eds. D. Schmidt, S. C. Schachter; Martin Dunitz, 2000). The literature, however, suggests that medicinal method of treating pyridoxine-dependent epilepsy is unsuitable for the treatment of other forms of epilepsy.

Vitamin B6 (pyridoxine) plays a crucial role in the metabolism of amino acids, proteins, carbohydrates, lipids, hormones and neuromediators (Lumeng L, Li T K. Mammalian vitamin $B_6$ metabolism: regulatory role of protein-binding and the hydrolysis of pyridoxine 5'-Phosphate in storage and transport. In: G. P. Tryfiates, ed. *Vitamin $B_6$, Metabolism and Role in Growth*. Food & Nutrition Press, Inc., Westport, Conn. 06880 USA, 1980: 27-51). The active form, pyridoxal-5'-phosphate (PLP), is the coenzyme of a large number of enzymes in mammalian tissues, including transaminases, decarboxylases and lyases, etc. Neurotransmitters (e.g. dopamine, norepinephrine, serotonin, tyramine, tryptamine, taurine, GABA (γ-aminobutyric acid), and indirectly acetylcholine) are also synthesized and/or metabolized by PLP-dependant enzymatic reactions (for reviews:Metzler, Biochemistry, Academic Press, 1977; Ebadi M., Regulation and function of pyridoxine phosphate in CNS. Neurochem.Int 1981, 3, 181-206; Leklem 1988 Vitamin B6 metabolism and function in humans. In: Clinical and physiological Application of vitamin B6 (Leklem & Reynolds eds.,) Alan R. Liss, NY, 1988; Shideler Ch. Vitamin B6: An Overview. *Am. J. Med. Technol.* 1983; 49:17-22).

SUMMARY OF THE INVENTION

There is provided in accordance with a preferred embodiment of the invention a composition for reducing the risk of epileptic occurrences and/or for alleviating epileptic phenomena in patients. In one preferred embodiment of the invention, the composition comprises a chemical compound consisting of a vitamin B6 moiety which is chemically linked to another chemical moiety selected from the group of antiepileptic drugs (AEDs) and anticonvulsive, neuroprotective, neurotransmitter and nootrope moieties. Preferably, the dosage of the composition is such that neither the vitamin B6 moiety nor the AED moiety/anticonvulsive moiety is present at more than the safe maximum dosage of that moiety. Such a compound may be represented by the formula:

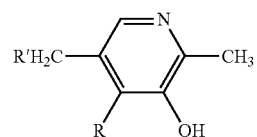

wherein R' represents the AED moiety or anticonvulsive, neuroprotective, neurotransmitter, or nootrope moiety and R is selected from the group consisting of —$CH_2OH$, —CHO and —$CH_2NH_2$; and pharmaceutically acceptable salts thereof.

In another preferred embodiment of the invention, the composition comprises a physical mixture of:
(a) a vitamin B6 compound having the formula:

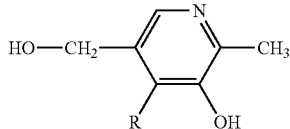

wherein R is selected from the group consisting of —CH$_2$OH, —CHO and —CH$_2$NH$_2$, and the vitamin B6 compound is employed in a single dosage no greater than its maximum safe dosage for single administration and its daily dose is no greater than maximum safe daily dosage, and
(b) an AED or anticonvulsive, neuroprotective drug, or nootrope compound, the AED or compound being employed in a dosage no greater than its maximum safe dosage for single administration, and its daily dose is no greater than maximum safe daily dosage.

In accordance with another preferred embodiment of the invention, a composition as set forth above is administered to a patient in such a manner that both the vitamin B6 compound and the AED, anticonvulsive, neuroprotective drug or nootrope compound are present in the patient in a single formulation.

The present invention also provides a method of treatment in which there is administered to patient in need of treatment at least one substance selected from the group consisting of pyridoxal, pyridoxamine and pyridoxine, their pharmaceutically acceptable functional derivatives and salts of any of these substances, in an amount which is equivalent to from about 2 to about 500 times the recommended daily dietary allowance of pyridoxine. Such at least one substance may be co-administered with at least one AED, anticonvulsive, neuroprotective drug or nootrope compound.

The present invention also provides a pharmaceutical composition which comprises a mixture, preferably an admixture, of at least the following components (i), (ii) and (iii), namely:
(i) at least one substance selected from the group consisting of pyridoxal, pyridoxamine and pyridoxine, their pharmaceutically acceptable functional derivatives and salts of any of these substances;
(ii) at least one AED or anticonvulsive, neuroprotective drug or nootrope compound; and
(iii) at least one pharmaceutically acceptable carrier, diluent, or excipient.

In a preferred embodiment of the invention, the mixture or admixture, and/or the individual components thereof, may be microencapsulated, using conventional micro encapsulation techniques, such as are disclosed in U.S. Pat. No. 6,156,347, the contents of which are incorporated herein by reference. Liposomes may also be employed for microencapsulation of the admixture or components thereof, as is known in the art.

As stated above, in one aspect the invention relates to the administration to a human subject of an amount of at least one of a defined group of substances in an amount not more than 500 mg/day, i.e. equivalent to about 2 to about 500 times the recommended daily dietary allowance of pyridoxine. In the present specification and claims, the recommended daily dietary allowance of pyridoxine means such allowance published by the Food and Nutrition Board of the National Academy of Sciences—National Research Council (U.S.A.), 1968 revision, as reproduced, e.g., in "The Pharmaceutical Basis of Therapeutics", 4$^{th}$ edition 1970, eds. Goodman and Gilman (The Macmillan Company). For convenience, the relevant data is reproduced below.

| Recommended Daily Dietary Allowance of Pyridoxine | | |
|---|---|---|
| | Age in Years (except for Infants) | Amount (mg) |
| Infants | up to 2 months | 0.2 |
| | 2-6 months | 0.3 |
| Children | 6-12 months | 0.4 |
| | 1-2 | 0.5 |
| | 2-3 | 0.6 |
| | 3-4 | 0.7 |
| | 4-6 | 0.9 |
| | 6-8 | 1.0 |
| | 8-10 | 1.2 |
| Males | 10-12 | 1.4 |
| | 12-14 | 1.6 |
| | 14-18 | 1.8 |
| | 18-22 | 2.0 |
| | 22-35 | 2.0 |
| | 35-55 | 2.0 |
| | 55-75+ | 2.0 |
| Females | 10-12 | 1.4 |
| | 12-14 | 1.6 |
| | 14-18 | 1.8 |
| | 16-18 | 2.0 |
| | 18-22 | 2.0 |
| | 22-35 | 2.0 |
| | 35-55 | 2.0 |
| | 55-75+ | 2.0 |
| Pregnancy | | 2.5 |
| Lactation | | 2.5 |

In accordance with a preferred embodiment of the invention, a method of reducing the risk of an epileptic occurrence in a high-risk human subject comprises the step of administering to the subject at least one substance selected from pyridoxal, pyridoxamine and pyridoxine, their pharmaceutically acceptable functional derivatives and salts of any of these substances, in an amount which is equivalent to from about 2 to about 500 times the recommended daily dietary allowance of pyridoxine.

The high-risk human subject may be, e.g., a pregnant or lactating woman with a family history of seizure disorders; a child with a family history of seizure disorders, particularly such a child within the age range of about 1-5 years, and then at puberty period 11-15; a child with a personal history of seizure episodes such as febrile, or breath-holding convulsions; a child with a congenital injury or asphyxia, particularly within the age of childhood or adolescence. The high-risk human subject may alternatively be, e.g. a person who has endured brain trauma, in which case pyridoxine is preferably administered in the amounts described above for a period of about 1-2 years after the episode. In another preferred embodiment of the invention, the high-risk human subject is one who had in the past undergone a course of treatment with at least one AED, which course of treatment has since been terminated. In such a case the course of administration of pyridoxine is preferably continued over a time period of about 1-2 years in a dosage 2-20 mg/kg, preferably 4-10 mg/kg. Preferably, the course of administration of pyridoxine is commenced immediately following termination of the course of AED treatment.

It is important to note that several specific forms of epilepsy, such as absence seizures, atypical absences and atonic seizures [ILAE revised classification of epileptic seizures (1981)] were shown not to be suitable for pyridoxine treatment.

In accordance with another preferred embodiment of the invention, a method of reducing the risk of epileptic attacks and alleviating epileptic occurrences, as well as alleviating the side effects of AEDs in a human subject, comprises the step of administering to the subject diagnosed as an epileptic patient, at least one substance selected from the group consisting of pyridoxal, pyridoxamine and pyridoxine, their pharmaceutically acceptable functional derivatives and salts of any of these substances, in an amount which is equivalent to from about 2 to about 500 times the recommended daily dietary allowance of pyridoxine, but does not exceed 500 mg of pyridoxine daily. In this embodiment of the invention, there is preferably co-administered with said at least one substance, at least one antiepileptic drug (AED), such as, by way of an example, at least one such drug selected from phenytoin or other hydantoins; phenobarbital or other barbiturates, primidone, carbamazepine and oxacarbamazepine, valproic acid or its derivatives; oxazolidines; benzo-diazepines; felbamate, gabapentin, lamotrigine, vigabatrin, adrenocorticotropic hormone (ACTH)("Antiepileptic Drugs", 4$^{th}$ Edition, Ed. by R. Levy, R. H. Mattson, B. S. Meldrum; Raven Press, NY, N.Y., 1995), as well as any other AED in use or potential AED. Neuroprotective drugs and nootropes, although not known as AEDs, may be used in place of the AEDs in the combination referred to above.

In accordance with a preferred embodiment of the invention, a method of preventing epileptic episodes and alleviating both epileptic episodes as well as the side effects of AEDs comprises the step of administering to the subject:

(a) at least one substance selected from the group consisting of pyridoxal, pyridoxamine and pyridoxine, their pharmaceutically acceptable functional derivatives and salts of any of these substances, in an amount which is equivalent to from about 2 to about 500 times the recommended daily dietary allowance of pyridoxine; in combination with (b) at least one AED, which may be selected from among those specified above.

In this embodiment of the invention, the human subject may be one who has to undergo a course of treatment with at least one AED and is at period of cancellation of AED treatment. Under these conditions the amount of AED administered daily in combination with vitamin B6 (or derivative thereof, as specified above) is preferably about 10-90% less than the amount of AED administered daily in the absence of vitamin B6 or a derivative thereof.

It will be appreciated that in those embodiments of the invention, in which an AED is co-administered with the at least one substance selected from pyridoxal, pyridoxamine and pyridoxine, their pharmaceutically acceptable functional derivatives and salts of any of these substances, then co-administration may take the form of separate administration of the two components. However, it will generally be more convenient to co-administer the two components in the form of an integrated composition as a tablet, capsule, dragee, or syrup or any other formulation.

Thus, there is provided in accordance with another preferred embodiment of the invention a pharmaceutical composition which comprises a mixture, preferably an admixture, of:

(a) at least one substance selected from pyridoxal, pyridoxamine and pyridoxine, their pharmaceutically acceptable functional derivatives and salts of any of these substances;

(b) at least one AED, neuroprotective drug or nootrope compound; and (c) at least one carrier, diluent or excipient.

In a preferred embodiment of the invention, the mixture or admixture, and/or the individual components thereof, may be microencapsulated, using conventional microencapsulation techniques, such as are disclosed in U.S. Pat. No. 6,156,347, the contents of which are incorporated herein by reference. Liposomes may also be employed for microencapsulation for the admixture or components thereof, as is known in the art. The carriers, diluents or excipients are those known in the pharmaceutical art, and will be selected, as is well known in that art, according to the relevant mode of administration, whether this be e.g. oral, parenteral, intranasal, rectal, transdermal or other acceptable mode of administration.

In the pharmaceutical compositions of the invention, the weight ratio of (a):(b) preferably lies in the range of about 1:0.1 up to about 1:1, starting of 1:0.1 at the beginning of treatment, from which time the dose of AED is gradually increased, if necessary, up to a stabilized ratio of about 1:1. Following a period of administration of (a) and (b) in a ratio of about 1:1, over the period of cancellation of treatment, the dose of (b) is gradually decreased and the ratio of (a):(b) is commensurately gradually altered from about 1:1 to about 1:0.1, whereby to gradually result in full replacement of (b) by (a), when the dose of (b) becomes equal to 0. These compositions will desirably be in the form of dosage units, which contain in total no more than the safe maximum adult daily dose of each of the components (a) and (b), preferably containing no more than about 500 mg of component (a), and no more than the typical adult daily dose of component (b).

It will be apparent to those skilled in the art that, insofar as, on the one hand, the invention relates to methods of treatment of individuals (including e infants and children), for whom the daily adult dose would be unsuitable, and on the other hand, the daily dose for adults and children may in any event be administered in divided doses, the dosage units of the invention may contain a fraction of the typical adult daily dose of component (b) and a fraction of the maximal daily dose of component (a). At least one AED may be, for example, selected from phenytoin or other hydantoins; phenobarbital or other barbiturates, primidone, carbamazepine and oxacarbamazepine, valproic acid or its derivatives; oxazolidines; benzodiazepines; felbamate, gabapentin, lamotrigine, vigabatrin, adrenocorticotropic hormone (ACTH), ("Antiepileptic Drugs", 4$^{th}$ Edition, Ed. by R. Levy, R. H. Mattson, B. S. Meldrum; Raven Press, NY, N.Y., 1995), as well as any other AED in use or potential AED. Neuroprotective compounds and nootropes, although not known as AEDs, may also be used as a component (b).

Insofar as reference has been made above to the typical adult daily dose of component (b) of the pharmaceutical compositions of the invention, it will be convenient to reproduce such data in respect of certain known AED (Antiepileptic Drugs 4$^{th}$ Ed. Ed. R. Levy, R. H. Mattson, B. S. Meldrum). It must be stressed, however, that the embodiments of the present invention that require the utilization of a known AED may equally utilize such drugs, which are not specified or tabulated herein, including potential AEDs, neuroprotective compounds or nootropes.

Typical Adult Daily Dose Of Some Known Anticonvulsant Drugs

| Name of Drug | Daily Dosage (mg/kg) |
|---|---|
| Carbamazepine | 5-20 |
| Valproic acid | 10-20 |

-continued

Typical Adult Daily Dose Of Some Known Anticonvulsant Drugs

| Name of Drug | Daily Dosage (mg/kg) |
|---|---|
| Phenytoin | 4-7 |
| Zonizamide | 8-12 |
| Clonazepam | 10-40 |

Hence, the present invention provides a new class of compositions, which reduce the risk of epileptic attacks and/or alleviate them, as well as reduce side effects of AEDs. The compositions of the present invention are characterized by the inclusion of a nontoxic component with neuroprotective and anticonvulsive properties, thus greatly reducing the chance of side effects. The activity of the compositions is sufficient so that they are as effective at relatively lower dosage levels than conventional anticonvulsants.

It should be noted that treatment of the type of epilepsy known as "pyridoxine-dependent epilepsy" by administration of pyridoxine has been reported in the art (Hunt et al. Pediatrics 1954; 13:140; Rosenberg In: Medical Genetics McKusic V A, ed. 1995: 73-8; Shideler Am. J. Med. Technol. 1983; 49:17-22; Scriver and Hutchison Pediatrics 1963; 31:240-50). The literature also suggests that medicinal method of treating pyridoxine-dependent epilepsy is unsuitable for the treatment of other forms of epilepsy. The present invention, in contrast, provides pyridoxine alone to be suitable for use in the prevention and treatment of initial forms of the disease as well as for prevention of relapse of forms of epilepsy other than pyridoxine-dependent epilepsy. In accordance with the invention, there is provided pyridoxine in combination with AEDs, either as a mixture or chemically bonded moieties, for the medicinal treatment of other than pyridoxine-dependent types of epilepsies at different stages of the disease. However, it should be noted that some specific forms of epilepsy, e.g. absence seizures, atypical absences and atonic seizures, which are unsuitable for pyridoxine treatment are also unsuitable for treatment by combinations of pyridoxine and AEDs either as mixtures or as chemically bounded moieties.

BEST MODE FOR CARRYING OUT THE INVENTION

Figure 1:
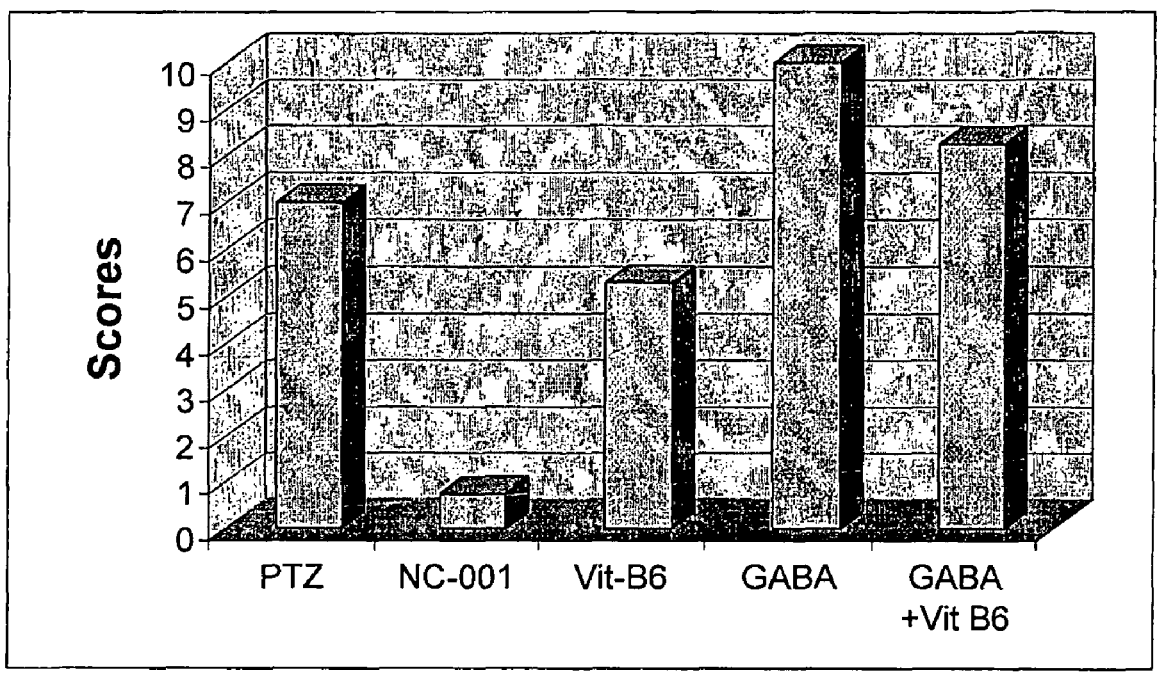
FIG. 1 depicts the scores of PTZ-induced convulsive reactions in genetically epilepsy-prone (EP) mice treated with either NC-001, vitamin B6, GABA, or a combination of vitamin B6 and GABA, as indicated.

In accordance with the present invention a class of compounds is set forth for reducing the risk of epileptic occurrences, for alleviating epileptic occurrences and reducing side effects of AED as well. In accordance with a preferred embodiment of the present invention, the compositions are compounds, which comprise (a) a vitamin B6 moiety, and (b) an AED moiety. The vitamin B6 moiety is linked chemically to the AED, neuroprotective or neurotransmitter compounds, or nootropes to give a new AED compound, which may be represented by the formula:

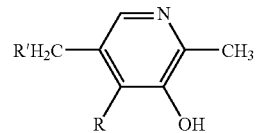

wherein R' represents the AED moiety and R is selected from the group consisting of —CH$_2$H, —CHO and CH$_2$NH$_2$, the composition being employed in a dosage no greater than its maximum safe dosage.

The AED moiety can be virtually any AED (or other compounds enlisted) which can be linked to the vitamin B6 moiety via attachment by etherification or the like to the —CH$_2$OH or —OH groups attached to the pyridine nucleus of the vitamin B6 moiety. Without limitation and by way of illustration and example, the AED moiety may be one which is obtained by reacting any AED of phenytoin or other hydantoins; phenobarbital or other barbiturates, primidone, carbamazepine and oxacarbamazepine, valproic acid or its derivatives; oxazolidines; benzo-diazepines; felbamate, gabapentin, lamotrigine, vigabatrin, adrenocorticotropic hormone (ACTH), ("Antiepileptic Drugs", 4$^{th}$ Edition, Ed. by R Levy, R. H. Mattson, B. S. Meldrum; Raven Press, NY, N.Y., 1995), as well as any other AED in use or potential AED with the aforementioned —CH$_2$OH group of vitamin B6. Neurotransmitters, neuroprotective compounds and nootropes, although not known as AED, may be used in place of the AEDs in the combination referred to above.

Thus, the preferred dosage range of the chemically coupled vitamin B6 moiety and the AED moiety is limited to no more than the safe maximum daily dose of each of the components. Such daily dose for adults and children may be administrated in the divided doses. It is advisable to stay within these ranges since the cited dosages provide significant alleviation of epileptic convulsions and/or serve to significantly reduce the risk of epileptic occurrence. According to the data obtained, chemically coupled vitamin B6 moiety with other anticonvulsive (or neuroprotective, neurotransmitter, nootrope) moieties are effective in low enough dosages so that adverse side effects are minimized or eliminated.

Without wishing to be bound by any particular theory, it is believed that most of AEDs as are set forth above, and other AED as well, pass through the blood-brain barrier in only small proportions, when present in the blood stream, and thus relatively high amounts of these compounds are needed in the blood stream to provide an effective amount of the AED within the brain. It is surmised that since vitamin B6 is easily absorbed into the gastrointestinal tract and passes relatively readily through the blood-brain barrier, by chemically linking AED and vitamin B6 moieties, the AED moieties will be more readily absorbed and carried across the blood-brain barrier, and thus a lower concentration of AED in the bloodstream will be required to reach an efficacious concentration of AED in the brain. This provides effective treatment for seizure disorders with less, or without the deleterious side effects, many of which are brought about by high concentrations of AED in the blood stream.

In accordance with another preferred embodiment of the present invention, vitamin B6 and anticonvulsant compounds can be administered separately or in physical mixtures to a patient in such a manner that both are presented to the subject at the same time. Preferably, the vitamin B6 and AED compounds are supplied in a single formulation. Preferred weight ratios of vitamin B6 to AED range from about 0.1:1 during dose-titration period at the beginning of treatment, up to about 1:1 when the treatment regime is stabilized. A gradual increase in the weight ratios of vitamin B6 to AED down to about 1.0:0.1 is recommended over the period of treatment cancellation, which is preferably ended by long-term treatment with pyridoxine alone.

The vitamin B6 compound has the formula:

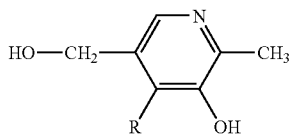

wherein R is selected from the group consisting of —CH$_2$OH, —CHO and —CH$_2$NH$_2$. The AED may be, for example, phenytoin or other hydantoins; phenobarbital or other barbiturates, primidone, carbamazepine and oxacarbamazepine, valproic acid or its derivatives; oxazolidines; benzodiazepines; felbamate, gabapentin, lamotrigine, vigabatrin, or adreno-corticotropic hormone (ACTH), or other AED. Neuroprotective or neurotransmitter compounds and nootropes, although not known as AEDs, may be used in place of the AEDs in the combination referred to above.

A more preferred range for the amount of the vitamin B6 compound is from about 2 mg to about 10 mg of vitamin B6 per kg body weight per day, and no more than the maximum daily doses allowable of each AED. The daily dose for adults and children may be administrated in the divided doses. It is very advisable to stay within these ranges since the cited dosages provide significant alleviation of epileptic seizures and/or serve to significantly reduce the risk of epileptic occurrence. Use of mixtures with pyridoxine allows decreasing doses of AED which are included into admixture, so that adverse side effects are minimized or eliminated.

The present invention will be better understood by reference to the illustrative examples, which follow wherein synthesis of a number of compounds in accordance with the present invention is set forth.

EXAMPLES

The synthesis protocols for conjugates of vitamin B6 with γ-aminobutyric acid (GABA), with kynurenic acid and with both GABA and kynurenic acid are exemplified below in Examples 1-3. However, it should be understood that similar procedures are also applicable for covalently linking pyridoxine or its derivatives to other natural or non-natural biologically active acids, e.g. anti-epileptic drugs or other neuroprotective compounds and nootropes, natural or synthetic neurotransmitters etc. For example, anti-epileptic drugs such as valproic acid, 1-(aminomethyl)cyclohexaneacetic acid (gabapentin) and 4-Amino-5-hexenoic acid (vigabactrin) may be chemically linked to pyridoxine by similar synthesis procedures as described in Examples 1 to 3. The end product is an ester such as, for example, the ester of valproic acid and vitamin B6 derivative shown below:

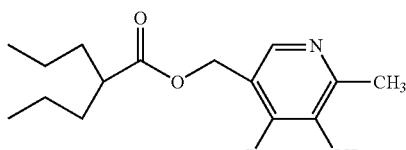

Ester of valproic acid and vitamin B6 derivative.

Other biologically active molecules, for example (amino-) anti-epileptic drugs such as 5-Ethyl-5-phenyl-2,4,6(1H,3H,5H)-pyrimidinetrione (Phenobarbital); 5,5-Diphenyl-2,4-imidazolidinedione (Phenyloin); 5-Ethyldihydro-5-phenyl-4,6(1H,5H) pirimidinedione (Primidone); 5H-Dibenz[b,f] azepine (Carbamazepine); 2-Phenyl-1,3-propanediol dicarbamate (Felbamate) etc. may also be chemically linked to pyridoxine. The procedure of synthesis of these molecules includes three stages as detailed below:

1. Synthesis of 5-Bromomethyl-3-hydroxy-4-hydroxymethyl-2-methylpyridine hydrobromide (3) as shown below in Example 1, step 2.
2. Synthesis of Li-amino-derivatives as shown below:

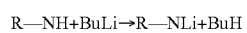

Wherein R—NH represents an anti-epileptic drug having an amino group.

A reaction wherein the R—NH drug is Phenyloin is exemplified below:

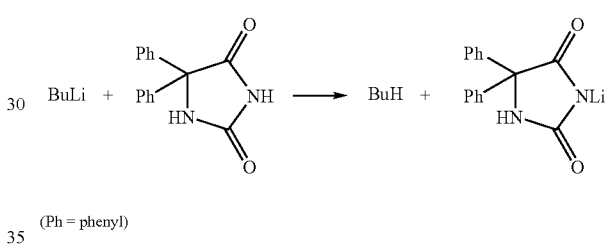

(Ph = phenyl)

3. Synthesis of pyridoxine-(amino-) drug conjugate:

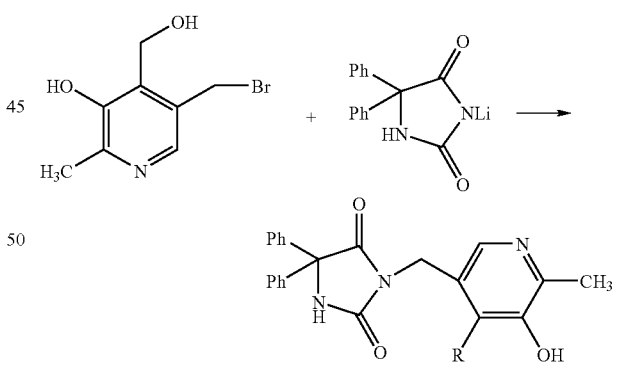

Example 1

Synthesis of [5-Hydroxy-6-methyl-4-(hydroxymethyl)-pyrid-3-yl]methyl-4-aminobutyrate, dihydrochloride (=B6-GABA)

The chemical structure of [5-Hydroxy-6-methyl-4-(hydroxymethyl)-pyrid-3-yl]methyl-4-aminobutyrate, dihydrochloride is:

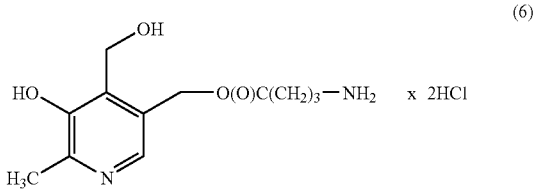

Synthesis of [5-Hydroxy-6-methyl-4-(hydroxymethyl)-pyridl-3-yl]methyl-4-aminobutyrate, dihydrochloride is a five-stage procedure. All synthesized compounds were characterized by NMR and mass spectroscopy analyses.

1. Synthesis of 3,4-Bis(bromomethyl)-5-hydroxy-6-methylpyridine (2)

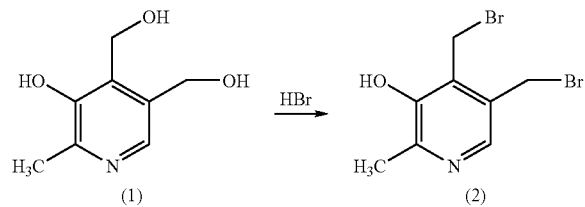

In the first stage Pyridoxine (1)(20 g, 0.097 mol) was refluxed in 48% hydrobromic acid (150 ml) for a 1 h. After crystallization at −15° C. the precipitate was separated, washed with acetone and dried. The yield was 25 g (68%).

MS (ES): m/z 295.95; 297.93 (M+H)$^+$.

2. Synthesis of 3-Bromomethyl-5-hydroxy-4-hydroxymethyl-6-methylpyridine hydrobromide (3)

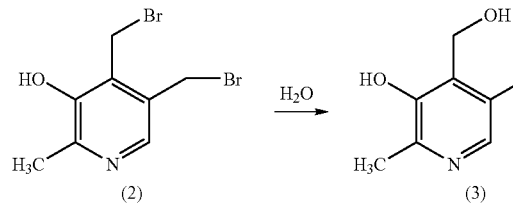

4,5-Bis(bromomethyl)-3-hydroxy-2-methylpyridine (2)(3 g, 0.008 mol) was stirred in water (24 ml) at 45-50° C. for 40 min. The solution was filtered and evaporated under vacuum. The obtained residue was crystallized from ethanol. The yield was 1.2 g (50%). The position of bromomethyl- in pyridine-ring was verified by qualitative analysis with 2,6-dichloroquinone-4-chloroimide (Harris and Folkers (1939) J. Am. Chem. Soc. 61: 247). M.p. 158-159° C.

$^1$H NMR (CD$_3$OD), δ: 2.62 (s., 3H), 4.72 (s., 2H), 5.18 (s., 2H), 8.30 (s., 1H). MS (ES): m/z 231.92; 233.91 (M+H)$^+$.

3. Synthesis of 4-(tert.) Buthyloxycarbonylaminobutiric acid (Boc-GABA)

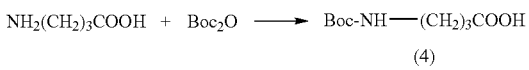

Where Boc$_2$O=[CO$_2$C(CH$_3$)$_3$]$_2$O 4-aminobutiric acid (GABA)(5.15 g, 0.05 mol) in 100 ml solution of water: 1N NaOH (1:1 v/v) was stirred in an ice-water bath. Di-tert.-butyl pyrocarbonate (11.99 g, 0.055 mol) was added at same temperature. The reaction mixture was stirred at room temperature for 1 hour. The solution was concentrated under vacuum to about 70 ml and cooled in an ice-water bath, covered with a layer of ethyl acetate (100 ml). Then it was acidified with a dilute solution of KHSO$_4$ to pH 2-3. The aqueous phase was extracted with ethyl acetate (2×50 ml). Ethyl acetate extracts were pooled, washed with water (2×70 ml), dried over anhydrous Na$_2$SO$_4$ and evaporated under vacuum. The yield was 10.00 g (98%).

$^1$H NMR (DMSO-d$_6$) δ: 1.37 (s., 9H), 1.60 (m., 2H), 2.19 (t., 2H), 2.92 (t., 2H). MS (ES): m/z 202.08 (M−H)$^{31}$.

4. Synthesis of [5-Hydroxy-6-methyl-4-(hydroxymethyl)-pyrid-3-yl]methyl-4-aminobutyrate

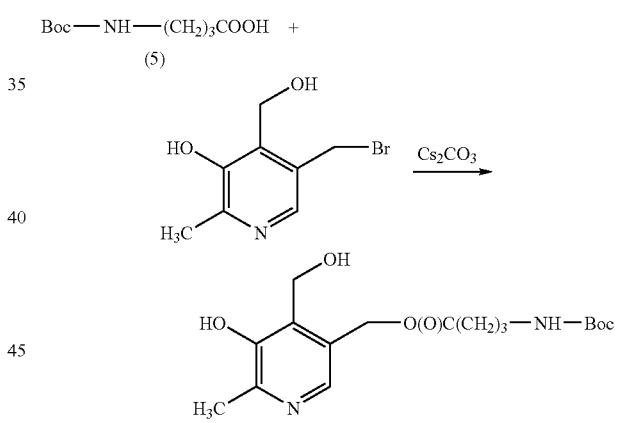

4-(tert.) buthyloxycarbonylaminobutiric acid (4)(2.03 g, 0.01 mol) and cesium carbonate (4.89 g., 0.015 mol) were stirred into dry DMSO (50 ml) at room temperature for 1.5 h under argon. 3-Bromomethyl-5-hydroxy-4-hydroxymethyl-6-methylpyridine hydrobromide (3) was added to the reaction mixture. The resulting brown solution was kept for 18 h. at room temperature. The next day the solution was diluted with water (150 ml) and extracted with ethyl acetate (3×50 ml). Ethyl acetate extracts were pooled, washed with water (3×50 ml), dried over anhydrous Na$_2$SO$_4$ and evaporated under vacuum. The crude precipitate was purified by column chromatography on silica gel with gradient. Eluent: chloroform (100%), chloroform:ethyl acetate (50%:50%), ethyl acetate (100%). The yield was 1.0 g (28%).

$^1$H NMR (DMSO-d$_6$) δ: 1.34 (s., 9H), 1.60 (m., 2H), 2.29 (t., 2H), 2.32 (s., 3H), 2.88 (t., 2H), 4.66 (s., 2H), 5.08 (s., 2H), 7.87 (s., 1H). MS (ES): m/z 355.28 (M+H)$^+$.

5. Synthesis of [5-Hydroxy-6-methyl-4-(hydroxymethyl)-pyrid-3-yl]methyl-4-aminobutyrate, dihydrochloride (6)

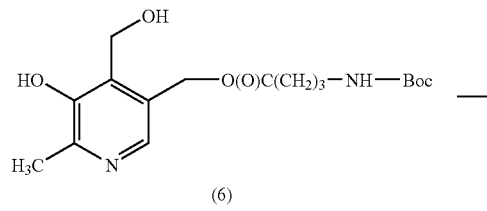

The solution of 5N HCl in ethyl acetate (7 ml) was added to solution of [5-Hydroxy-6-methyl-4-(hydroxymethyl)-pyrid-3-yl]methyl-4-aminobutyrate (5) (1.8 g, 5.08 mmol) in ethyl acetate (20 ml) at 0° C. The reaction mixture was stirred at 0-5° C. for 2 hours. Residual compound was separated and crystallized from the mixture of methanol-ether. The yield was 0.7 g. (42%).

$^1$H NMR (CD$_3$OD) δ: 1.95 (m., 2H), 2.64 (t., 2H), 2.65 (s., 3H), 2.99 (t., 2H), 5.09 (s., 2H), 5.38 (s., 2H), 8.22 (s., 1H). MS (ES): m/z 255.13 (M+H)$^+$.

Example 2

Synthesis of [3-(5-Hydroxy-6-methyl-4-(hydroxymethyl)pyrid-yl]methyl-2-[(4-hydroxy)quinoline]carboxylate (=B6-Kyn)

The chemical structure of [3-(5-Hydroxy-6-methyl-4-(hydroxymethyl)pyrid-yl]methyl-2-[(4-hydroxy)quinoline]carboxylate is:

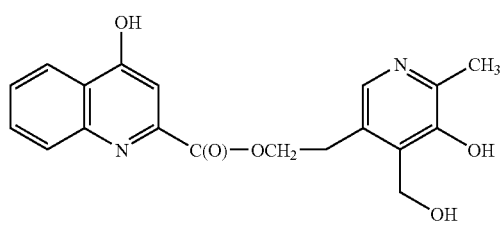

A mixture of 4-hydroxyquinoline-2-carboxylic acid hydrate (kynurenic acid (7)) (1.80 g, 8.70 mmol) and cesium carbonate (4.25 g, 13.05 mmol) were stirred in dried DMSO (70 ml) at room temperature for 1.5 h under argon. Followed by addition of 3-Bromomethyl-5-hydroxy-4-hydroxymethyl-6-methylpyridine hydrobromide (3)(3.58 g, 11.42 mmol). The obtained brown solution was kept for 18 h at room temperature, then diluted with water (200 ml) and extracted with ethyl acetate (12×150 ml). After crystallization at 5° C. the precipitate was separated, washed with ethyl acetate, ether and dried. The yield was 0.25 g. (7.8%).

$^1$H NMR (DMSO-d$_6$) δ 2.36 (s, 3H), 4.77 (s, 2H), 5.47 (s, 2H), 6.60 (s, 1H), 7.37 (t, 1H), 7.69 (t, 1H), 7.89 (d, 1H), 8.05 (s, 1H), 8.06 (d, 1H). MS (ES): m/z 341.17 (M+H)$^+$.

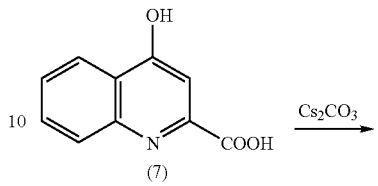

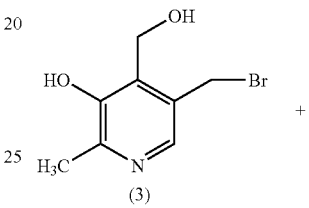

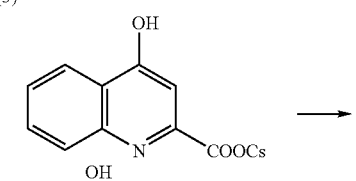

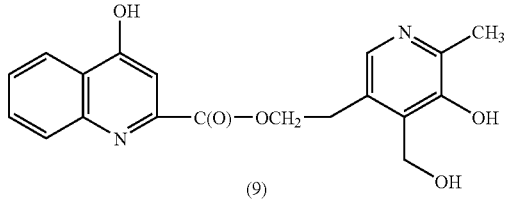

Example 3

Synthesis of 5-Hydroxy-4-hydroxymethyl-6-methyl-pyrid-3-yl)methyl [4-(4-hydroxyquinoline-2-carbonylamino)]butyrate (B6-GABA-Kyn)

The chemical structure of 3-Hydroxy-4-hydroxymethyl-2-methyl-pyrid-5-yl)methyl [4-(4-hydroxyquinoline-2-carbonylamino)]butyrate is:

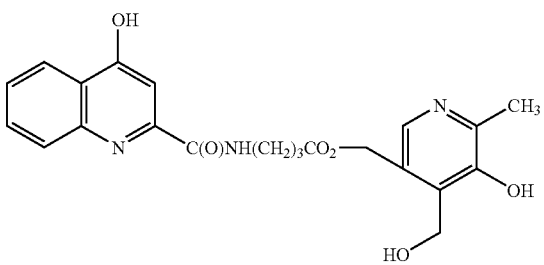

1. Synthesis of 4-(4-Hydroxyqunoline-2-carbonylamino)butanoic acid (10)

BSA (N,O-bis(trimethylsilyl)acetamide)(3.26 ml, 13.20 mmol) was added to a suspension of 4-aminobutanoic acid (GABA)(0.62 g, 6.00 mmol) in dry dichloromethane (10 ml) and the mixture was stirred for 6 hours at 50° C. The resulting solution was added to a mixed anhydride prepared from kynurenic acid (7) (0.95 g, 5.00 mmol), $Et_3N$ (1 ml), EtOCOCl (0.5 ml, 5.25 mmol) in dry DMF (10 ml) incubated at −20° C. for 20 min. The reaction mixture was stirred at −5° C. for 2 hours and kept at 4° C. for further 18 hours. Water (50 ml) and ethyl acetate (30 ml) were then added. The compound (10) in mixture with kynurenic acid was separated from the water layer (0.5 g).

$^1$H NMR (DMSO-$d_6$) δ 1.79 (m, 2H), 2.28 (t, 2H), 6.67 (s, 1H), 7.33 (t, 1H), 7.67 (t, 1H), 7.91 (d, 1H), 8.05 (d, 1H), 9.00 (s, 1H), 11.78 (s, 1H); m/z 273.06 (M−H)⁻.

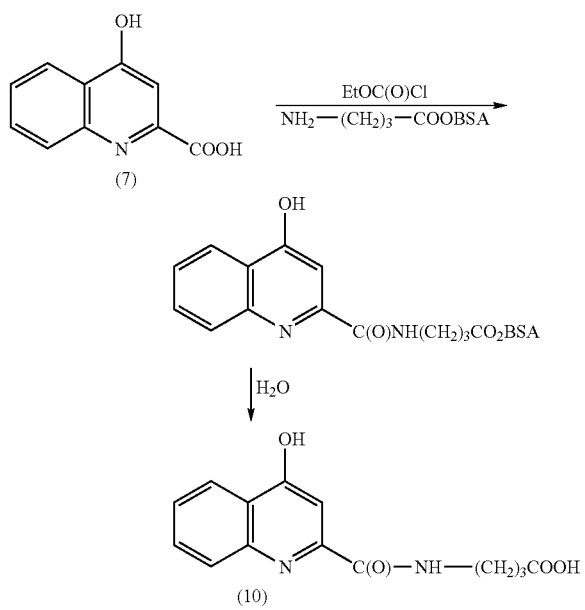

2. Synthesis of 5-Hydroxy-4-hydroxymethyl-6-methyl-pyrid-3-yl)methyl [4-(4-hydroxyquinoline-2-carbonylamino)]butyrate (11)

The mixture of compound (10)(0.47 g, 1.71 mmol) and cesium carbonate (0.89 g, 2.74 mmol) was stirred for 1.5 hours in dried DMSO (40 ml) at room temperature under argon. Compound (3)(0.72 g, 2.30 mmol) was then added. The resulting brown solution was kept for 18 hours at room temperature, before being diluted with water (120 ml) and extracted with ethyl acetate (5×100 ml). After crystallization at 5° C. the precipitate was separated, washed with ethyl acetate, ether and dried. The yield was 0.04 g.

$^1$H NMR (DMSO-$d_6$) δ: 1.82 (m, 2H), 2.48 (s, 3H), 2.50 (t, 2H), 4.79 (s, 2H), 5.28 (s, 2H), 6.79 (s, 1H), 7.37 (t, 1H), 7.69 (t, 1H), 7.93 (d, 1H), 8.05 (s, 1H), 8.06 (d, 1H); 9.03 (s, 1H); m/z 424.08 (M−H)⁻.

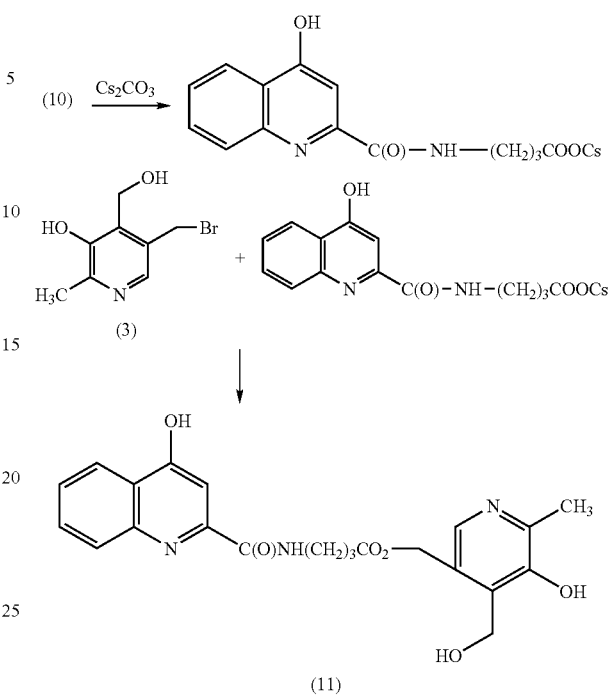

Example 4

Anticonvulsive Effect of Pyridoxine Chemically Linked with GABA (NC-001 Compound)

Anticonvulsive effect of Pyridoxine chemically linked with GABA, [5-hydroxy-6-methyl-4-(hydroxymethyl)-pyrid-3-yl]methyl-4-aminobutyrate, dihydrochloride (=B6-GABA conjugate; also referred to as NC-001 compound), was examined in an animal model of genetic epilepsy.

The animal model used is epilepsy-prone (EP) subline of mice that was selectively bred from a strain of BALB/c mice (Dolina et al. in Epilepsia (1993) 43: 33-42). EP mice are characterized as having genetically increased susceptibility to seizures.

EP mice were subjected to seizure induction by intraperitoneal (i.p.) injection of pentylenetetrazol (PTZ) 50-60 mg/kg dissolved in saline. The EP animals were i.p. treated with the tested compound(s) 10 to 60 minutes prior to the PTZ injection.

The tested compounds were the following:
1) NC-001 10 mg/kg
2) Pyridoxine hydrochloride (=Vitamin B6) 10 mg/kg
3) GABA 10 mg/kg
4) Separately injected Vitamin B6 and GABA, 10 mg/kg each.

A group of EP animals injected with PTZ only, with no further treatment, served as a control group.

The intensity of the PTZ-induced convulsive reaction for each group was evaluated in scores according to the following scale:

Intensity of PTZ-induced Convulsive Reaction in Scores
1. A few myoclonic jerks (less than 10)
2. Less than 20 jerks
3. Less than 30 jerks
4. 30-40 jerks/jerks and jumps/short partial convulsions.

5. Uninterrupted jerks/series of jerks and jumps/repeated partial convulsions
5.5 Abortive generalized convulsions
6. Single generalized convulsive attack
7. Series of jerks, jumps & single generalized convulsive attack; single generalized convulsions with further motor excitation
7.5 Severe prolonged generalized convulsions
8. Repeated generalized convulsions
9. Series of jerks/jumps & repeated convulsions
10. Status epilepticus
12. Lethal convulsions In each group of EP animals, convulsive reactions were recorded during the first 30 minutes following administration of the seizure inducer.

As shown in FIG. 1, the conjugated compound, NC-001, that was injected 30 minutes prior to the PTZ injection, provided almost a complete protection against the convulsive symptoms. Four out of the six tested mice did not show any convulsive reaction, while the other two animals had only few convulsive jerks. Under the same experimental setting, GABA alone, as well as GABA and Vitamin B6 injected simultaneously as combination of both, did not show any anticonvulsive effect at the tested dose of 10 mg/kg. Vitamin B6 by itself showed some protection against PTZ-induced generalized convulsions.

Example 5

The Anticonvulsive Effect of NC-001 is Dose Dependent

In order to further characterize the anticonvulsive activity of the compounds of the invention, different doses of NC-001, namely pyridoxine chemically linked with GABA were examined.

Genetically epilepsy-prone (EP) BALB/c mice, 3-5 animals in a group, were i.p. administered with either 5 mg/kg, 7.5 mg/kg or 10 mg/kg of NC-001 thirty minutes prior to i.p. injection of PTZ (60 mg/kg). The numbers of seizures were then recorded for each animal during 30 minutes following the PTZ injection. The intensity of convulsive reaction was scored for each of the treatment groups.

Figure 2:
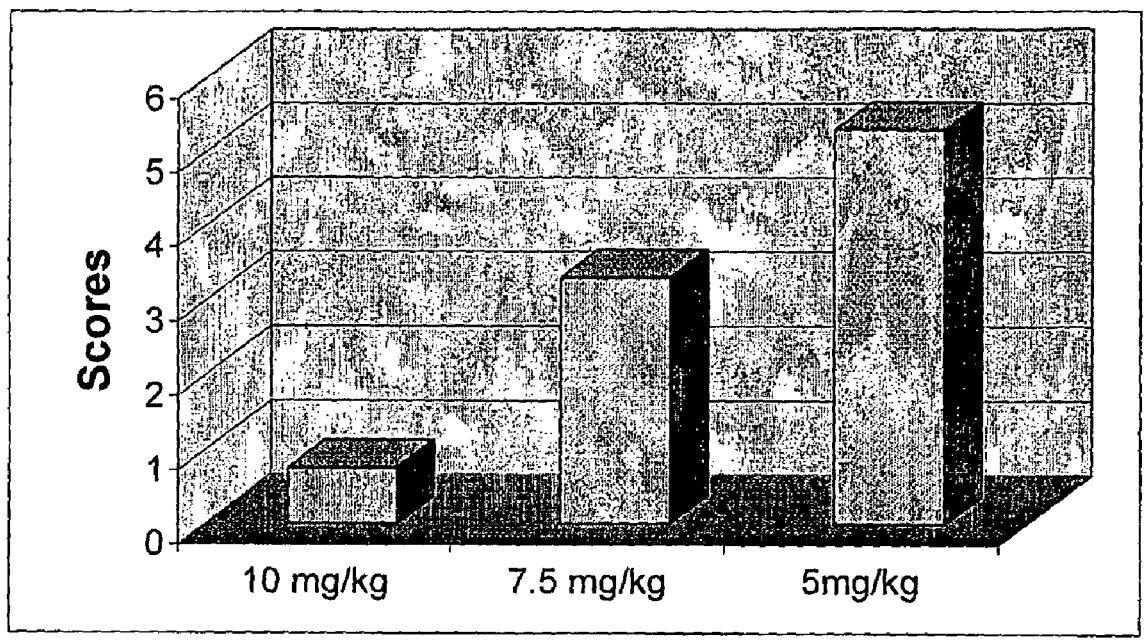
FIG. 2 depicts the PTZ-induced convulsive response in genetically epilepsy-prone (EP) BALB/c mice treated with 5 mg/kg, 7.5 mg/kg or 10 mg/kg NC-001.

As can be seen in FIG. 2, the NC-001 compound demonstrated a dose-dependent anti-convulsive protective effect. Five mg/kg intraperitoneally (i.p.) injected NC-001 already induced protective effect; only two of the four EP mice treated with this compound exhibited generalized convulsions, while the other two animals had a number of jerks. At a dosage of 7.5 mg/kg, NC-001 prevented generalized PTZ-induced convulsions in all three treated EP mice, though numerous jerks were observed in all of them. NC-001 injected at a dose of 10 mg/kg, completely prevented generalized convulsive reactions, while single jerks occurred in one of EP mice.

Conclusion: NC-001 effectively protects genetically epilepsy-prone animals, which are characterized by enhanced seizure predisposition, from PTZ-induced convulsions. The anticonvulsive effect is dose dependent.

Example 6

The NC-001 Compound Demonstrated Anti-convulsive Effect when Orally Administered In order to test the ability of the vitamin B6-GABA conjugated compound to cross the GI barrier, epilepsy-prone (EP) mice were orally administered with NC-001.

A group of 12 female EP mice were i.p. treated with 50 mg/kg PTZ to induce seizures. Thirty minutes prior to PTZ administration, NC-001 at the dose of 30 mg/kg was orally administered to four of the animals (=treated group), the other eight animals were treated with vehicle only and served as a control group. All twelve animals were scored, during 30 minutes following i.p. PTZ administration, for intensity of convulsive reactions (see table of convulsive reaction scores as appear above in Example 4).

Figure 3:
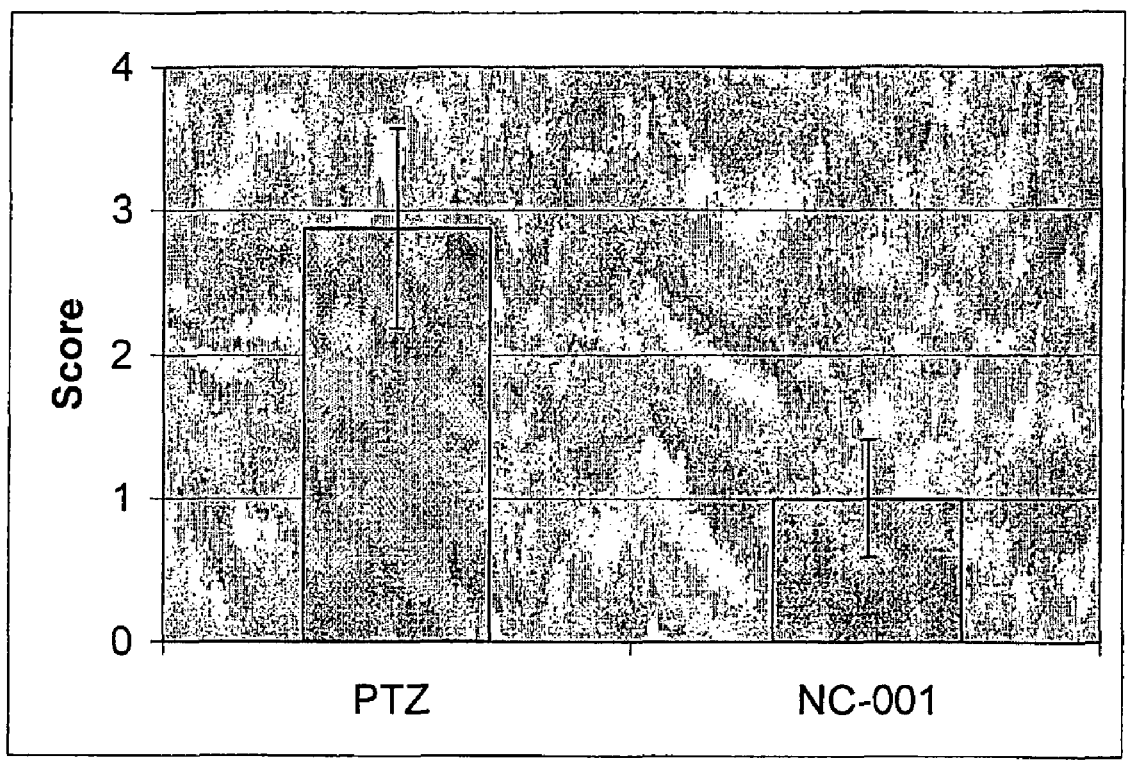
FIG. 3 depicts the anti-convulsive effects of NC-001 administered orally to genetically epilepsy-prone (EP) mice.

As can be seen in FIG. 3, a significant protective effect was demonstrated in the EP mice orally administered with the NC-001 compound.

Example 7

Physical Admixture of AED with Pyridoxine and Testing Thereof

A physical admixture of (a) pyridoxine hydrochloride and (b) an AED is prepared. It is administered simultaneously or substantially simultaneously to patients suffering from epilepsy. The weight ratio of (a):(b) is in the range of about 0.1:1 to 1:1 near the beginning of treatment and 1:0.1 near the end of treatment. These compositions will desirably be in the form of dosage units, which contain in total no more than the safe maximum adult daily dose of each of the components (a) and (b), preferably containing no more than about 500 mg of component (a) at a daily dose 2-10 mg/kg, particularly 4-7 mg/kg, and no more than the typical adult daily dose of component (b).

The admixture reduces the risk of epileptic occurrence or alleviates epileptic occurrence and diminishes of AED toxicity. An admixture may be administered in the form of tablets, capsules, syrups, microcapsules, liposomes, or any other pharmaceutically acceptable forms.

Example 8

Pyridoxine-Supplemented Phenyloin as an Example of Co-Administration of AED with Pyridoxine Phenyloin (PHT) is prescribed for medication of generalized tonic-chronic generalized convulsions, complex partial seizures and simple partial seizures. The efficacy of the mixtures in accordance with present invention was demonstrated in the animal model of genetic epilepsy—audiogenic sensitive rats, which reacted with generalized convulsions to sound-stimulation. In the experiments, intensity of 100 db sound stimulation was used.

The seizure sensitivity to the sound stimulation was tested in two groups of audiogenic sensitive rats chronically treated with PHT. One group of rats was long-term treated with pyridoxine (75 mg/kg in drinking water). The second group included pyridoxine-untreated rats. The initial injection of PHT 75 mg/kg was followed by 12 successive injections of PHT 50 mg/kg once a day. Eleven rats were used in each group. The incidence and intensity of sound-induced convulsions were comparatively estimated in both groups of rats at the $13^{th}$ and $14^{th}$ days, so that each of animals was tested twice.

The experiments showed that only two of 22 tests (9%) resulted in sound-induced convulsions in the group of pyridoxine-treated EP rats, while 6 convulsive reactions (27.3%) were obtained in the group of animals treated with PHT only (pyridoxine untreated animals). Moreover, under same dosage of PHT given chronically, the intensity of sound-induced convulsions estimated in scores was significantly lower in the pyridoxine-treated animals in comparison to the untreated EP-rats. Hence, it was shown that co-administration of high-dose pyridoxine significantly increased the efficacy of chronic PHT administration in epileptic animals.

Example 9

Reduction of PHT Toxicity by Co-administration of Pyridoxine

Sacrificed animals of both the pyridoxine-treated and untreated groups described in Example 8 were examined. The signs of PHT toxicity such as a compressed liver, bleeding areas in the lungs and enlarged adrenals were found in all 11 EP-rats chronically treated with PHT alone, but not in those which were given the same dose of PHT co-administrated with pyridoxine (75 mg/l in drinking water). Hence, co-administration of pyridoxine reduced the toxicity of PHT given chronically over the period of 12 days at the dosage 50 mg daily following the initial injection at the dose 75 mg/kg.

Example 10

Use of Compositions

The compositions of each of above-described Examples are utilized in a dosage no greater than the maximum safe dosage for the individual components to treat patients to alleviate and retard epileptic convulsions. At this concentration range each of the compositions shows significant activity in retardation and alleviation of epilepsy.

The above examples illustrate the synthesis and efficacy of various compositions in accordance with the present invention.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features herein before set forth.

The invention claimed is:

1. A compound of the formula (I):

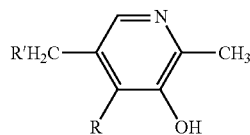

wherein R' represents an anti-epileptic drug moiety or an anticonvulsive drug moiety; wherein the drug moiety is selected from the group consisting of phenytoin and other hydantoins; phenobarbital and other barbiturates; primidone, carbamazepine and oxacarbamazepine, valproic acid or its derivatives; oxazolidines; benzo-diazepines; felbamate; gabapentin; lamotrigine; vigabatrin and adrenocorticotropic hormone (ACTH); γ-aminobutyric acid and kynurenic acid; and
R is selected from the group consisting of —CH$_2$OH, —CHO and —CH$_2$NH$_2$; or pharmaceutically acceptable salts thereof.

2. The compound according to claim 1, wherein said anti-epileptic drug is selected from the group consisting of phenytoin and other hydantoins; phenobarbital and other barbiturates, primidone, carbamazepine and oxacarbamazepine, valproic acid or its derivatives; oxazolidines; benzo-diazepines; felbamate, gabapentin, lamotrigine, vigabatrin and adrenocorticotropic hormone (ACTH).

3. The compound according to claim 1, wherein R' represents a moiety of γ-aminobutyric acid and kynurenic acid.

4. A pharmaceutical composition comprising a therapeutically effective amount of the compound of the formula (I):

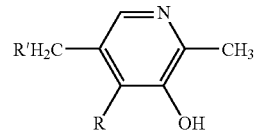

and a pharmaceutically acceptable carrier or excipient, wherein R' represents an anti-epileptic drug moiety or an anticonvulsive drug moiety; wherein the drug moiety is selected from the group consisting of phenytoin and other hydantoins; phenobarbital and other barbiturates; primidone, carbamazepine; and oxacarbamazepine, valproic acid or its derivatives; oxazolidines; benzo-diazepines; felbamate; gabapentin; lamotrigine; vigabatrin and adrenocorticotropic hormone (ACTH); γ-aminobutyric acid and kynurenic acid; and
R is selected from the group consisting of —CH$_2$OH, —CHO and —CH$_2$NH$_2$; or pharmaceutically acceptable salts thereof.

5. The pharmaceutical composition according to claim 4, wherein the compound of the formula (I) having R' in an amount which is no greater than the maximal safe amount for a single administration of the attached anti-epileptic drug moiety or anticonvulsive drug moiety.

6. A method of treatment of epilepsy comprising administering to an individual in need thereof a therapeutically effective amount of a compound of the formula (I):

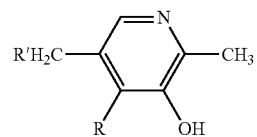

wherein R' represents an anti-epileptic drug moiety or an anticonvulsive drug moiety; wherein the drug moiety is selected from the group consisting of phenytoin and other hydantoins; phenobarbital and other barbiturates; primidone, carbamazepine and oxacarbamazepine, valproic acid or its derivatives; oxazolidines; benzo-diazepines; felbamate; gabapentin; lamotrigine; vigabatrin and adrenocorticotropic hormone (ACTH); γ-aminobutyric acid and kynurenic acid; and
R is selected from the group consisting of —CH$_2$OH, —CHO and —CH$_2$NH$_2$; or pharmaceutically acceptable salts thereof.

7. A method for preventing epileptic episodes, alleviating epileptic episodes and/or reducing side effects of anti-epileptic drugs comprising the step of administering to a subject a therapeutically effective amount of a compound of the formula (I):

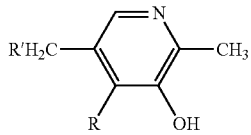

wherein R' represents an anti-epileptic drug moiety or an anti-convulsive drug moiety; wherein the drug moiety is selected from the group consisting of phenytoin and other hydantoins; phenobarbital and other barbiturates; primidone, carbamazepine and oxacarbamazepine, valproic acid or its derivatives; oxazolidines; benzo-diazepines; felbamate; gabapentin; lamotrigine; vigabatrin and adrenocorticotropic hormone (ACTH); γ-aminobutyric acid and kynurenic acid; and R is selected from the group consisting of —$CH_2OH$, —CHO and —$CH_2NH_2$; or pharmaceutically acceptable salts thereof.

8. The method according to claim 6, wherein said compound is orally administered.

* * * * *